US010602743B2

(12) United States Patent
Cordova-Kreylos et al.

(10) Patent No.: US 10,602,743 B2
(45) Date of Patent: *Mar. 31, 2020

(54) **METHOD OF INDUCING DROUGHT/SALT TOLERANCE USING *BACILLUS MEGATERIUM***

(71) Applicant: Marrone Bio Innovations, Inc., Davis, CA (US)

(72) Inventors: Ana Lucia Cordova-Kreylos, Davis, CA (US); Carly Todd, Davis, CA (US); Debora Wilk, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 441 days.

This patent is subject to a terminal disclaimer.

(21) Appl. No.: 14/992,295

(22) Filed: Jan. 11, 2016

(65) Prior Publication Data

US 2016/0113288 A1  Apr. 28, 2016

Related U.S. Application Data

(63) Continuation-in-part of application No. 14/738,772, filed on Jun. 12, 2015, now Pat. No. 9,801,386, which is a continuation of application No. 13/832,407, filed on Mar. 15, 2013, now Pat. No. 9,084,428.

(60) Provisional application No. 61/683,154, filed on Aug. 14, 2012, provisional application No. 62/106,634, filed on Jan. 22, 2015.

(51) Int. Cl.
*A01N 63/00* (2020.01)
*A01N 63/02* (2006.01)
*C12N 1/20* (2006.01)
*C12R 1/11* (2006.01)

(52) U.S. Cl.
CPC ............ *A01N 63/00* (2013.01); *A01N 63/02* (2013.01); *C12R 1/11* (2013.01)

(58) Field of Classification Search
None
See application file for complete search history.

(56) References Cited

U.S. PATENT DOCUMENTS

| | | | |
|---|---|---|---|
| 5,403,583 | A | 4/1995 | Liu et al. |
| 6,096,306 | A | 8/2000 | Bravo |
| 6,245,717 | B1 | 6/2001 | Dean et al. |
| 7,429,477 | B2 | 9/2008 | Johnson |
| 9,084,428 | B2 | 7/2015 | Asolkar et al. |
| 2002/0119124 | A1 | 8/2002 | Da Luz |
| 2010/0261694 | A1 | 10/2010 | Lam et al. |
| 2012/0077677 | A1 | 3/2012 | Willms et al. |
| 2012/0157304 | A1 | 6/2012 | Johnson |
| 2015/0047070 | A1* | 2/2015 | Day .................. C12N 15/8273 800/278 |

FOREIGN PATENT DOCUMENTS

| | | |
|---|---|---|
| EP | 2496536 A2 | 9/2012 |
| WO | 94/21795 A1 | 9/1994 |
| WO | 1996028031 A1 | 9/1996 |
| WO | 2004002227 A1 | 1/2004 |
| WO | 2011124554 A2 | 10/2011 |
| WO | 2014009402 A1 | 1/2014 |

OTHER PUBLICATIONS

Omar et al. Plant pathology 55.1 (2006): 92-99.*
Vary (Microbiology (1994), 140, 1001-1013).*
Sousa et al. (Journal of Microbiological Methods 95 (2013) 327-335).*
Marulanda, et al. Journal of Plant Growth Regulation 28.2 (2009): 115-124.*
Changsong Zou et al: "Bacillus megaterium strain XTBG34 promotes plant growth by producing 2-pentylfuran", The Journal of Microbiology, vol. 48, No. 4, Aug. 1, 2010 (Aug. 1, 2010) pp. 460-466.
Database WPI Week 201049 Thomson Scientific, London, GB; AN 2010-J13789 XP002750959 & WO 20101079763 A1 (Snow Brand Seed Co Ltd) Jul. 15, 2010 (Jul. 15, 2010)* abstract *.
Database WPI Week 200966 Thomson Scientific, London, GB; AN 2009-L87431 XP002750961, & KR 2009 3077528 A (Univ Kyungpook Nat Ind Academic Coop) Jul. 15, 2009 (Jul. 15, 2009)* abstract *.
Malanicheva I A et al: "Antimicrobial Activity of Bacillus megaterium Strains", Microbiology, Nauka/Interperiodica, MO, vol. 81, No. 2, Apr. 18, 2012 (Apr. 18, 2012), pp. 178-185.
European Search Report 13829973.0 dated Nov. 27, 2015.
Chau et al., "Role of RecA in the Protection of DNA Damage by UV-A in *Escherichia coli*." Journal of Experimental Microbiology and Immunology (Apr. 2008) vol. 12, pp. 39-44.
Janousek et al. "Control of brown rot and shot hole in almond." 2009 field trial, Department of Plant Pathology UC Davis (2010) pp. 1st-4th.
Eppinger et al. Genome sequences of the biotechnologically important Bacillus megaterium strains QM B1551 and DSM319, J. Bacteriol. (Epub Jun. 24, 2011) vol. 193(16), pp. 4199-4213.
Genbank CP001982.1 (last viewed on Nov. 12, 2014).
Kanjanamaneesthian et al. "Bacillus megaterium Suppresses Major Thailand Rice Diseases" Asian Journal of Food and Agro-industry (2009) Special Issue, S154-S159.
Askoy, H.M., et al. (2008) Isolation of Bacillus Megaterium from Aphis Pomi (Homoptera:Aphididae) and Assessment of its Pathogenicity. Journal of Plant Pathology. 90(3) 449-452.
Huang, Y. et al. (201 0). Characterisation of volatiles produces from Bacillus Megaterium YFM3.25 and their Nematicidal Activity Against Meloidogyne Incognita. Eur. I Plant Pathol126:417-422.
Oliveira, D. F. et al. (2007). Selection of rhizobacteria able to produce metabolites active against Meloidogyne exigua. European Journal of Plant Pathology, 119.477-479.

(Continued)

Primary Examiner — Charles Logsdon
(74) Attorney, Agent, or Firm — Chainey P. Singleton; Ying-Horng Liu

(57) ABSTRACT

Provided are method of induce plant drought and/or salinity tolerance using microbes such as *Bacillus*, and particularly *Bacillus megaterium* cultures responsible for controlling plant drought and/or salinity tolerance.

5 Claims, 2 Drawing Sheets

(56) References Cited

OTHER PUBLICATIONS

Martin, L. et al. (1995). Cloning and Sequencing of the pac gene Encoding the Penicillin G Acylase of Bacillus Megaterium ATCC 14945. FEMS Microbiology Letters, 125:287-292.

Neipp, P. W. et al. (1999). Evaluation of biocontrol activity of rhizobacteria from Beta vulgaris against Heterodera schachtii. Journal of nematology, 31(1), 54-61.

Padgham, J.L. et al. (2007). Biological control potential and modes of action of Bacillus megaterium against Me/pidogyne graminico/a on rice. Crop prot. 26, 971-977.

Pandey, R et al. (2011). Enhanced Tolerance of Mentha Arvensis Against Meloidogyn Incognita (Kofoid and White) Chitwood through Mutualistic Endophytes and PGPRs. Journal of Plant Interactions, 6:4, 247-253.

Suga, K. et al. (1990). Reaction Kinetics and Mechanism of Immobilized Penicillin Acylase from Bacillus Megaterium. Annals New York Academy of Sciences. 808-815.

Vary, P. (1994). Prime Time for Bacillus Megaterium. Microbiology, 140:1001-1013.

Vary, P. et aL (2007) Bacillus Megaterium—from Simple Soil Bacterium to Industrial Protien Production Host. Appl. Microbial Biotechnol, 76:957-967.

El-Hadad, M.L. et al. (2011). The Nematicidal Effect of Some Bacterial Biofertilizers on Meloidogyne Incognita in Sandy Soil. Brazilian Journal of Microbiology, 42:105-113.

Gu, Y. et al. (2007). Evaluation and identification of potential organic nematicidal volatiles from soil bacteria. Soil Biology and Biochemistry, 39, 2567-2575.

* cited by examiner

METHOD OF INDUCING DROUGHT/SALT TOLERANCE USING *BACILLUS MEGATERIUM*

CROSS REFERENCE TO RELATED APPLICATIONS

This application claims priority to non-provisional patent application of U.S. Provisional Patent Application Ser. No. 62/106,634, filed Jan. 22, 2015; and is a continuation-in-part and claims benefit of U.S. application Ser. No. 14/738,772, filed on Jun. 12, 2014, which is a continuation application and claims benefit of Ser. No. 13/832,407, filed Oct. 24, 2011, now U.S. Pat. No. 9,084,428, which claims priority to and the benefit under 35 U.S.C. § 119(e) of U.S. Provisional Application No. 61/683,154, filed Aug. 14, 2012. All of which are hereby incorporated by reference in their entirety.

TECHNICAL FIELD

The present disclosure is in the field of bioactive compositions from a *Bacillus* strain that increases plant drought and/or salt tolerance.

BACKGROUND

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. There are several well-known examples of microbial natural products that are successful as agricultural insecticides (Thompson et al., 2000; Arena et al., 1995; Krieg et al. 1983).

The development of a microbial pesticide starts with the isolation of a microbe in a pure culture. It then proceeds with efficacy and spectrum screening using in vitro, in vivo or pilot scale trials in a greenhouse and in the field. At the same time, active compounds produced by the microbe are isolated and identified. For the commercialization of a microbial pesticide, the microbe has to be economically produced by fermentation at an industrial scale, and formulated with a biocompatible carrier and approved additives to increase efficacy and to maximize the ease of application.

Uses of *Bacillus Megaterium* and Products Produced Therefrom

*Bacillus megaterium* is a Gram-positive bacterium that grows in simple media and on more than 62 out of 95 carbon sources, such as tricarboxylic acid cycle intermediates (e.g., formate and acetate), and forms spores mainly under aerobic conditions (see, for example, Vary, 2007). It has been found in a variety of habitats, such as soil, seawater, sediment, rice paddies, honey, fish, and dried food.

*Bacillus megaterium* has been found to have a number of different uses. Specifically, it produces a variety of industrial enzymes such as penicillin acylase, various amylases, and glucose dehydrogenase (reviewed in, Vary, 2007). Additionally, a fermentation of *B. megaterium* ATCC 19213 grown to stationary phase was found to produce N-Deoxyschizokinen, a siderophore, which was identified as 4-[(3(acetylhydroxyamino)propyl)amino]-2-[2-[(3-(acetylamino)propyl) amino]-2-oxoethyl]-2-hydroxy-4-oxo-butanoic acid (Hu X and Boyer G. L, 1995). Schizokinen, a citrate-containing dihydroxamate, a siderophore has been produced by *B. megaterium* and *Anabaena* sp (Plowman J. E. et al 1984). The involvement of the citrate α-hydroxycarboxylate moiety in iron chelation was investigated by comparing the iron binding behavior of schizokinen with that of acetylschizokinen, a derivative in which the citrate hydroxyl group was modified by acetylation.

Another set of uses for products derived from *Bacillus megaterium* has been medicinal uses. BMG 59-R2, a peptide antibiotic, has been reported from *B. megaterium* (FERM-p 6177). The compound also inhibits alkaline phosphatase and tumour growth (Japan. Pat., 83 164 561. (1983)). Fermentation culture of *B. megaterium* in the presence of ansatrienin produces T23V and T23VI (Damberg, M. et at 1982). These compounds belong to the class of macrolides antibiotics, which also exhibit antitumor activity. A nucleoside named oxetanocin was isolated from *B. megaterium* NK84-0218 and the structure was determined to be 9-[(2R, 3R,4S)-3,4-bis(hydroxymethyl)-2-oxetanyl]adenine by X-ray crystallographic analysis (Shimada N. et a., 1986). Oxetanocin showed activity against herpes simplex virus-II (DNA virus) at 5.8 pg/well (50% inhibition of cytopathic effect), while the cytotoxicity against Vero cells was 132.6 µg/well (50% inhibition of cell growth). Later, the derivatives of oxetanocin such as oxetanocins H, X, G and 2-aminooxetanocin A (Shimada N. et a., 1987) are isolated from the same strain which showed antiviral activities against herpes simplex virus type-II (HSV-II) and antiviral activities against human immunodeficiency virus. *B. megaterium* IFO 12108 (Nakahama, K. et al., 1981) was used for the microbial transformation of anamtiocin, an antitumor antibiotic produced by *Nocardia* sp. C-15003 (N-1). Ansamitocin P-3 was converted into 15-hydroxyansamitocin P-3 (PHO-3), and 15-epi-15-hydroxyansamitocin P-3 (epi-PHO-3), by using *B. megaterium* (Izawa M. et al., 1981). The microbial conversion product of P-3, has greater antitumor activities against P 388 and L 1210 than the substrate P-3.

Various isolates of *Bacillus megaterium* have been used as insecticides, bactericides, fungicides and nematicides (see, for example, Aksoy, H. M. 2008; U.S. Pat. Nos. 6,599,503, 7,906,131, 7,935,360). Some of these *B. megaterium* isolates have been used in combination with other bacteria to treat sludge and wastes such as *Artemisia annua* residue, flue dust, bran powder, feces of livestock and poultry, peat, and crop straw (see, for example, U.S. Pat. No. 7,279,104).

SUMMARY

In an aspect, the invention relates to a method for increasing disease tolerance in a plant. The method includes applying a composition to the plant in an amount effective for increasing drought and/or salt tolerance in the plant. The composition includes an isolated culture of *Bacillus* strain.

In one aspect, the *Bacillus* is a *B. megaterium* strain having the identifying characteristics of *B. megaterium* strain H491 (NRRL Accession No. B-50769), *Bacillus megaterium* strain MO 18 (NRRL Accession No. B-50770) and *Bacillus megaterium* strain J142 (NRRL Accession No. B-50771), or a strain derived from one of said strains (e.g., a mutant strain). Also provided is a substantially pure culture, or whole cell broth comprising said microorganism or cell fraction, supernatant, filtrate, extract, compound or metabolite derived therefrom.

Also provided are microbial compositions that include a microbial strain of the invention or a culture thereof. Such microbial compositions according to some preferred embodiments may comprise an agriculturally effective amount of an additional compound or composition, in which the additional compound or composition may be a fertilizer, an acaricide, a bactericide, a fungicide, an insecticide, a microbicide, a nematicide, or a pesticide. In some other preferred embodiments, the microbial compositions may further include a carrier. In yet other preferred embodiments, the carrier may be a plant seed. In certain embodiments of this aspect, the microbial composition is prepared as a formulation that can be an emulsion, a colloid, a dust, a granule, a pellet, a powder, a spray, an emulsion, or a solution. In some other preferred embodiments, the microbial compositions may be seed coating formulations. In yet another aspect, plant seeds that are coated with a microbial composition in accordance with the present invention are also provided.

In another aspect, there are provided methods for treating plant seeds. Such methods include exposing or contacting the plant seeds with a microbial strain according to the present invention or a culture thereof.

DETAILED DESCRIPTION

Figure 1:
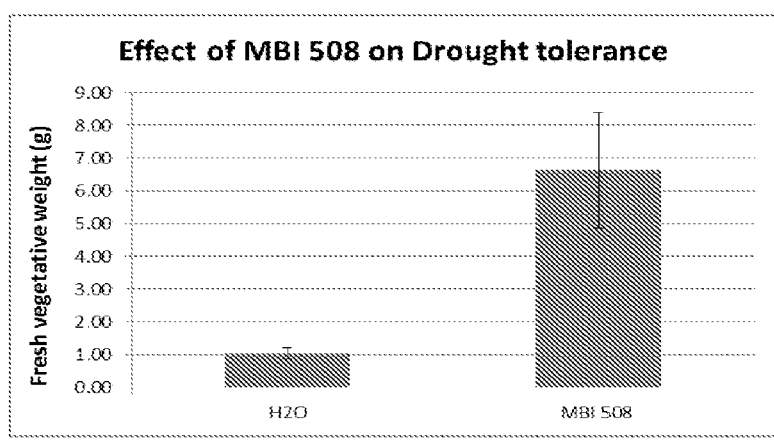
FIG. 1 denotes a plot of tomato vegetative weight versus application of *B. megaterium* strain (A.K.A. MBI-508) and control (water).
Figure 2:
FIG. 2 denotes a picture of tomato plants with (left three columns) and without (right three columns) *B. megaterium* strain application under drought conditions.

While the compositions and methods heretofore are susceptible to various modifications and alternative forms, exemplary embodiments will herein be described in details. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit, unless the context clearly dictates otherwise, between the upper and lower limit of that range and any other stated or intervening value in that stated range, is included therein. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or from the medium used to culture or grow said organism.

As defined herein, "whole broth culture" refers to a liquid culture containing both cells and media. If bacteria are grown on a plate the cells can be harvested in water or other liquid, whole culture.

The term "supernatant" refers to the liquid remaining when cells that are grown in broth or harvested in another liquid from an agar plate are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal and particularly, nematicidal activity.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods and electrophoretic methods.

A "carrier" as defined herein is an inert, organic or inorganic material, with which the active ingredient is mixed or formulated to facilitate its application to plant or other object to be treated, or its storage, transport and/or handling.

The term "modulate" as defined herein is used to mean to alter the amount of drought tolerance.

As used herein, "water stress" refers to the conditions or environments that provide improper (less/insufficient) amounts of water than that needed for adequate/successful growth and development of plants/crops thereby subjecting the plants to stress and/or damage to plant tissues and/or negatively affecting plant/grain/crop yield.

As used herein, "drought stress" refers to a period of dryness (acute, intermittence, or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

The term "drought tolerance" refers to the ability of a plant to endure or resist drought conditions or stress. "Drought" refers to a condition in which a plant is subjected to osmotic stress or reduced water potential. For example, drought may be caused by lack of available water for a period of time. Drought conditions may be assessed by comparing the amount of water required for growth or maturation a plant to the amount of water available to the plant. Drought conditions may be caused, for example, by lack of rainfall or irrigation, relative to the amount of water used internally or transpired by a plant.

The term "drought resistance" refers to the ability of a plant to develop fewer symptoms of water stress (e.g., lower productivity, leaf loss, death) than the corresponding control plant when grown under identical conditions of water stress. Drought resistance includes complete resistance to the effects of drought (no loss of productivity) or varying degrees of resistance manifested as decreased symptoms or longer survival.

Phenotypic assessment of symptoms may be used to determine whether, and to what extent, a plant is suffering from drought. For example, drought tolerance and/or resistance may be assessed by observing and rating wilting, growth arrest, death, productivity, leaf loss (e.g., leaf rolling, leaf distortion, leaf drop, leaf scorch), stem or twig dieback, photosynthetic efficiency, flowering, vegetative weight, and yield level in a plant. In addition, drought tolerance and/or resistance of a plant may be assessed, for example, by biochemical or nucleic acid based assays to measure expression or activation of specific response genes in the plant.

Drought tolerance and/or resistance is increased in a plant if the plant demonstrates less severe symptoms of stress caused by the drought. For example, drought tolerance and/or resistance is increased if wilting, growth arrest, death, leaf loss (e.g., leaf rolling, leaf distortion, leaf drop, leaf scorch), and/or stem or twig dieback is decreased when compared to a corresponding control plant when grown under identical conditions without application of the inventive method or composition. Other examples of an increased drought tolerance and/or resistance include an increase in vegetative weight, productivity, plant vigor, photosynthetic efficiency, flowering, and/or yield level in a plant when compared to a corresponding control plant when grown under identical conditions without application of the inventive method or composition.

Accordingly, the term "increasing" drought tolerance and/or resistance refers to an increase in drought tolerance and/or resistance of an impacted plant treated with a method or composition of the invention, in which the tolerance and/or resistance is greater than the drought tolerance and/or resistance in a corresponding control plant grown under identical conditions and water stress.

The increase drought tolerance and/or resistance may be an increase that is 2, 3, 4, 5, 6, 7, 8, 9, 10, 15, 20, 25, 30 (or more) fold greater as compared to the tolerance and/or resistance of a corresponding control plant grown under identical conditions and water stress. For example, a plant having increased drought tolerance and/or resistance as compared to the control plant may have 10%, 15%, 20%, 25%, 30%, 40%, 50%, 60% 70%, 75%, 80%, 90%, 100% or greater drought tolerance and/or resistance than the corresponding control plant grown under identical conditions without application of the inventive method or composition.

A "plant" as used herein refers to any type of plant, such as a tree, shrub, flower, herb, vine, or grass. The term "plant" also refers to any part of the plant, for example, to a whole plant, a plant part, a plant cell, or a group of plant cells, such as plant tissue, or progeny of same. Plantlets are also included within the meaning of "plant." Plants include, for example, any gymnosperms and angiosperms, both monocotyledons and dicotyledons, and trees.

A "control plant", as used in the present disclosure, provides a reference point for measuring changes in phenotype of the subject plant, may be any suitable plant cell, seed, plant component, plant tissue, plant organ or whole plant. A control plant can comprise, for example, (a) a wild-type plant or cell not under drought stress, i.e., of the same genotype as the starting material which resulted in the subject plant or cell; (b) a plant or cell which is genetically identical to the subject plant or cell but which is not exposed to the same treatment (e.g., drought stress) as the subject plant or cell or (c) the subject plant or cell itself, under conditions in which it has not been exposed to a particular treatment such as, for example, a fertilizer or combination of fertilizers and/or other chemicals.

As used herein, "MBI-303", "MBI-508", "303", "508" and *Bacillus megaterium* are synonymous and can be used interchangeably.

General Methods

The organisms are cultivated in nutrient medium using methods known in the art. In particular, isolation, its metabolites/compositions and other method of uses for *B. megaterium* can be found in US patent application Publication Number US-2014-0051571-A1, which is incorporated herein by reference in its entirety.

As noted above, compounds or metabolites can be obtained, are obtainable or are derived from an organism having the identifying characteristics of a *B. megaterium*, or alternatively from any other microorganism. The methods comprise growing these organisms (e.g., in culture) and obtaining the compounds and/or compositions by isolating these compounds from the culture of these organisms.

The organisms can be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation can take place in suitable nutrient medium comprising carbon and nitrogen sources and inorganic salts, using procedures known in the art. Suitable media are available from commercial sources or can be prepared according to published compositions.

After cultivation, a supernatant, filtrate and/or extract of or derived from *B. megaterium* can be used in formulating a pesticidal composition.

Alternatively, after cultivation, the compounds and/or metabolites may be extracted from the culture broth.

The extract can be fractionated by chromatography. Chromatographic fractions can be assayed for drought tolerance inducer agents using methods known in the art. This process can be repeated one or more times using the same or different chromatographic methods.

Compositions

Compositions may comprise whole cell broth cultures, liquid cultures, or suspensions of a strain from a *B. megaterium*, as well as supernatants, filtrates or extracts obtained from a strain of a *B. megaterium*, or the supernatant, filtrate and/or extract or one or more metabolites or isolated compounds derived from a strain of a *B. megaterium* or combinations of the foregoing.

The compositions set forth above can be formulated in any manner. Non-limiting formulation examples include but are not limited to Emulsifiable concentrates (EC), Wettable powders (WP), Soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), etc. In any formulation described herein, percent of the active ingredient is within a range of 0.01% to 99.99%.

The compositions may be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower.

A composition may comprise gel-encapsulated active ingredient(s). Such gel-encapsulated materials can be prepared by mixing a gel-forming agent (e.g., gelatin, cellulose, or lignin) with a culture or suspension of live or inactivated

*B. megaterium*, or a cell-free filtrate or cell fraction of a *B. megaterium* culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may be combined with another microorganism, pesticide (e.g., nematicide, fungicide, insecticide), drought tolerance inducer agent, or drought tolerant transgenic plants. The microorganism can include but is not limited to an agent derived from *Bacillus* sp. (e.g., *Bacillus firmus, Bacillus thuringiensis, Bacillus pumilus, Bacillus licheniformis, Bacillus amyloliquefaciens, Bacillus subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp (*S. bikiniensis, S. costaricanus, S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplrnium, Neobulgaria, Daldinia, Aspergillus, Chaetomium, Lysobacter* spp, *Lachnum papyraceum, Verticillium suchlasporium, Arthrobotrys oligospora, Verticillium chlamydosporium, Hirsutella rhossiliensis, Pochonia chlamydosporia, Pleurotus ostreatus, Omphalotus olearius, Lampteromyces japonicas, Brevudimonas* sp., *Muscodor* sp.

The agent can also be a natural oil or oil-product having nematicidal, fungicidal insecticidal and/or drought inducing activity (e.g., paraffinic oil, tea tree oil, lemongrass oil, clove oil, cinnamon oil, citrus oil including but not limited to bitter orange, orange, lemon; rosemary oil, pyrethrum, allspice, bergamot, blue gum, camomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, saponins). Furthermore, the pesticide can be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin can include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a *Reynoutria* extract.

The fungicide can also be a multi-site non-inorganic, chemical fungicide selected from the group consisting of chloronitrile, quinoxaline, sulphamide, phosphonate, phosphite, dithiocarbamate, chloralkythios, phenylpyridinamine, cyano-acetamide oxime.

As noted above, the composition can further comprise a nematicide. This nematicide can include but is not limited to chemicals such as organophosphates, carbamates, and fumigants, and microbial products such as avermectin, *Myrothecium* sp. Biome (*Bacillus firmus*), *Pasteuria* spp., *Paecilomyces*, and organic products such as saponins and plant oils.

The compositions can be applied using methods known in the art. Specifically, these compositions can be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment of the plants and plant parts with the compositions set forth above may be carried out directly or by allowing the compositions to act on their surroundings, habitat or storage space by, for example, immersion, spraying, evaporation, fogging, scattering, painting on, injecting. In the case that the composition is applied to a seed, the composition may be applied to the seed as one or more coats prior to planting the seed, or applied as a slurry or dust when planting, using one or more coats using methods known in the art. The seed in a particular embodiment may be a genetically modified seed.

Plants be treated include but are not limited to: (A) Major edible food crops, which include but are not limited to (1) Cereals (e.g., African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, *sorghum, Sorghum* spp., rye, spelt wheat); (2) Fruits (e.g., abiu, acerola, achacha, African mangosteen, alpine currant, ambarella, American gooseberry, American persimmon, apple, apricot, arazá, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blueberried honeysuckle, borojó, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee *Arabica*, coffee robusta, Costa Rica pitahaya, currants, custard apple, date, date-plum, dog rose, dragonfruit, durian, elderberry, elephant apple, Ethiopian eggplant, European nettle tree, European wild apple, feijoa, fig, gac, genipapo, giant granadilla, gooseberry, goumi, grape, grapefruit, great morinda, greengage, guava, hardy kiwi, hog plum, homed melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain papaya, mountain soursop, mulberry, naranjilla, natal plum, northern highbush blueberry, olive, otaheite gooseberry, oval kumquat, papaya, para guava, passionfruit, pawpaw, peach, peach-palm, pear, pepino, pineapple, pitomba *Eugenia luschnathiana*, pitomba *Talisia esculenta*, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L. chinense*), yellow mombin, yellow pitaya, yellow-fruited strawberry, guava, (3) Vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, barbados gooseberry, beet, beet root, bitter gourd, bitter vetch, bitterleaf, black mustard, black radish, black salsify, blanched celery, breadfruit, broad bean, broccoli, brussels sprout, Buck's horn plantain, buttercup squash, butternut squash, cabbage, caigua, calabash, caraway seeds, carob, carrot, cassabanana, cassava, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, good king henry, grass pea, groundnut, guar bean, horse gram, horseradish, hyacinth bean, iceplant, Indian fig, Indian spinach, ivy gourd, Jerusalem artichoke, jicama, jute, kale, kohlrabi, konjac, kurrat, leek, lentil, lettuce, Lima bean, lotus, luffa, maca, maize, mangel-wurzel, mashua, moso bamboo, moth bean, mung bean, napa cabbage, neem, oca, okra, oldham's bamboo, olive, onion, parsnip, pea, pigeon pea, plantain, pointed gourd, potato, pumpkins, squashes, quinoa, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop *trapa bicornis*, water *caltrop trapa* natans, water morning slory, watercress, welsh onion, west African okra, west Indian gherkin, white goosefoot, white yam, winged bean, winter purslane, yacón, yam, yard-long bean, zucchinietables); (4) Food crops (e.g., abiu, acerola, achacha, ackee, African mangosteen, African rice, agate, air potato, alpine currant, *Amaranthus* app., Ambarrella, American gooseberry, American groundnut, American persimmon, antroewa, apple, apricot, arazá, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, betel nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blue-berried honeysuckle, borojó, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassava, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (*Arabica* and *Robusta* types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, durum wheat, eddoe, eggplant, einkorn wheat, elderberry, elephant apple, elephant foot yam, elephant garlic, emmer wheat, endive, enset, Ethiopian eggplant, European nettle tree, European wild apple, feijoa, fig, finger millet, florence fennel, fluted gourd, foxtail millet, gac, garden rocket, garlic, genipapo, geocarpa groundnut, giant granadilla, good king henry, gooseberry, goumi, grape, grapefruit, grass pea, great morinda, greengage, groundnut, grumichama, guar bean, guava, hairy crabgrass, hardy kiwi, hog plum, homed melon, horse gram, horse mango, horseradish, hyacinth bean, iceplant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, luffa, lychee, maca, maize, malay apple, mamey saptoe, mammee apple, mangelwurzel, mango, mangosteen, maprang, marang, mashua, medlar, melon, Mirabelle plum, miracle fruit, monk fruit, monkey jack, moriche palm, moso bamboo, moth bean, mountain papaya, mountain soursop, mulberry, mung bean, mushrooms, nance, napa cabbage, naranjilla, natal plum, neem, northern highbush blueberry, oat, oca, oil palm, okra, oldman's bamboo, olive, onion, orange, otaheite gooseberry, oval kumquat, papaya, para guava, parsnip, passionfruit, pawpaw, pea, peach, peach-palm, pear, pearl millet, pepino, pigeon pea, pineapple, Pitomba (*Eugenia luschnathiana, Talisia esculenta*), plantain, plum, pointed gourd, pomegranate, pomelo, potato, proso millet, pulasan, pumpkins and squashes, purple chokeberry, quince, quinoa, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, sorghum, Sorghum spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, tef, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacón, yam, yangmei, yard-long bean, yellow mombin, yellow pitaya, yellow-fruited strawberry guava, zucchini; (B) Other edible crops, which includes but is not limited to (1) Herbs (e.g., *Absinthium*, alexanders, basil, bay laurel, betel nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, ginseng, gray santolina, herb hyssop, holy basil, hop, jasmine, kaffir lime, lavender, lemon balm, lemon basil, lemon grass, lovage, marjoram, mint, oregano, parsley, peppermint, perilla, pot marigold, rooibos, rosemary, sage, shiny-leaft buckthorn, sorrel, spearmint, summer savory, tarragon, Thai basil, valerian, watercress, wild betel, winter savory, yerba mate); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard); (2) Medicinal plants (e.g., *absinthium*, alfalfa, aloe vera, anise, artichoke, basil, bay laurel, betel leaf, betel nut, bilberry, black cardamom, black mustard, black pepper, blue gum, borojó, camomlie, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray santolina, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red acacia, red currant, rooibos, safflower, sage, shiny-leaf buckthorn, sorrel, spilanthes, star anise, tarragon, tea, turmeric, valerian, velvet bean, watercress, white mustard, white sapote, wild betel, wolfberry (*Lycium barbarum, L. chinense*), yerba mate); (3) Stimulants (e.g., betel leaf, betel nut, cacao, chili pepper (*Capsicum annuum, C. baccatum, C. chinense, C. frutescens, C. pubescens*), chili peppers, coffee, coffee (*Arabica*, Robusta), cola nut, khat, Liberian coffee, tea, tobacco, wild betel, yerba mate); (4) Nuts (e.g., almond, betel nut, Brazil nut, cashew nut, chestnut, Chinese water chestnut, coconut, cola nut, common walnut, groundnut, hazelnut, Japanese stone oak, macadamia, nutmeg, paradise nut, pecan nut, pistachio nut, walnut); (5) Edible seeds (e.g., black pepper, Brazil nut, chilacayote, cola nut, fluted gourd, lotus, opium, quinoa, sesame, sunflower, water caltrop (*Trapa bicornis, T. natans*); (6) Vegetable oils (e.g., black mustard, camelina, castor bean, coconut, cotton, linseed, maize, neem, niger seed, oil palm, olive, opium, rapeseed, safflower, sesame, soybean, sunflower, tung tree, turnip); (7) Sugar crops (e.g., Asian palmyra palm, silver date palm, *sorghum*, sugar beet, sugarcane); (8) Pseudocereals (e.g., *Amaranthus* spp., buckwheat, quinoa, red amaranth); (9) Aphrodisiacs (e.g., borojó, celery, durian, garden rocket, ginseng, maca, red acacia, velvet bean); (C) Non-food categories, including but not limited to (1) forage and dodder crops (e.g., agate, alfalfa, beet, broad bean, camelina, catjang, grass pea, guar bean, horse gram, Indian barnyard millet, Japanese barnyard millet, lespedeza, lupine, maize, mangel-wurzel, mulberry, niger seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassava, maize, rapeseed, *sorghum*, soybean, Sudan grass, sugar beet, sugarcane, wheat); (4) Alcohol production, (e.g., barley, plum, potato, sugarcane, wheat, *sorghum*); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray santolina, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, sunn hemp, trefoil, velvet bean, vetch); (7) Erosion prevention (e.g., bamboo, cocoplum); (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, chrysanthemum, daffodil, dahlia, freesia, gerbera, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, chrysanthemum, cocoplum, common lavender, crocus, daffodil, dahlia, freesia, gerbera, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia, almond, apple, apricot, arborvitae nigra american, arborvitae, ash, aspen, azalea, baldcypress, beautybush, beech, birch, black tupelo, blackberry, blueberry, boxwood, buckeye, butterfly bush, butternut, camellia, catalpa, cedar, cherry, chestnut, coffeetree, crab trees, crabapple, crapemyrtle, cypress, dogwood, douglasfir, ebony, elder American, elm, fir, forsythia, ginkgo, goldenraintree, hackberry, hawthorn, hazelnut, hemlock, hickory, holly, honeylocust, horsechestnut, hydrangea, juniper, lilac, linden, magnolia, maple, mockorange, mountainash, oak, olive, peach, pear, pecan, pine, pistache, planetree, plum, poplar, pivet, raspberry, redbud, redcedar, redwood, rhododendron, rose-of-sharon, sassafras, sequoia, serviceberry, smoketree, soapberry, sourwood, spruce, strawberry tree, sweetshrub, sycamore, tuliptree, viburnum, walnut, weigela, willow, winterberry, witchhazel, zelkova; (E) Turf which includes but is not limited to Kentucky bluegrass, tall fescue, Bermuda grass, zoysia grass, perennial ryegrass, fine fescues (e.g.; creeping red, chewings, hard, or sheep fescue).

The compositions may also be applied to the soil using methods known in the art. Such methods include but are not limited to fumigation, drip irrigation or chemigation, soil incorporation, soil drenching, seed treatment and dressing, bare root dip.

Drought Tolerance Uses

The compositions disclosed herein, in particular, *Bacillus megaterium* and/or a whole cell broth, supernatant, filtrate, extract, compound, metabolite or cell fraction obtained from a culture of *B. megaterium*, can be used to modulate drought tolerance property of plants, e.g. crops such as fruit (e.g., strawberry), vegetable (e.g., tomato, squash, pepper, eggplant), or grain crops (e.g., soy, wheat, rice, corn), tree, flower, ornamental plants, shrubs (e.g., cotton, roses), bulb plant (e.g., onion, garlic) or vine (e.g., grape vine). The compositions can also be used to modulate the germination of a seed(s) in a plant(s) under increased drought or salt stress conditions.

The compositions disclosed herein, or formulated product, can be used alone or in combination with one or more other components as described below, such as growth promoting agents and/or anti-phytopathogenic agents in a tank mix or in a program (sequential application called rotation) with predetermined order and application interval during the growing season. When used in a combination with the above-mentioned products, at a concentration lower than recommended on the product label, the combined efficacy of the two or more products (one of which is the said composition disclosed herein) is, in certain embodiments, greater than the sum of each individual component's effect. Hence, the effect is enhanced by synergism between these two (or more) products, and the risk for the development of pesticide resistance among the plant pathogenic strains is reduced.

The composition can be applied by root dip at transplanting, specifically by treating a fruit or vegetable with the composition by dipping roots of the fruit or vegetable in a suspension of said composition (about 0.25 to about 1.5% and more particularly about 0.5% to about 1.0% by volume) prior to transplanting the fruit or vegetable into the soil.

Alternatively, the composition can be applied by drip or other irrigation system. Specifically, the composition can be injected into a drip irrigation system. In a particular embodiment, the composition is applied at a concentration of $1\times10^8$ CFU/ml in a volume of approximately 11 to approximately 4 quarts per acre.

In yet another embodiment, the composition can be added as an in-furrow application. Specifically, the composition can be added as an in-furrow spray at planting using nozzles calibrated to deliver a total output of 2-6 gallons/acre. Nozzles are placed in the furrow opener on the planter so that the pesticide application and seed drop into the furrow are simultaneous.

Mixtures of the disclosed compositions with, for example, a solid or liquid adjuvant are prepared in known manner. For example, mixtures can be prepared by homogeneously mixing and/or grinding the active ingredients with extenders such as solvents, solid carriers and, where appropriate, surface-active compounds (surfactants). The compositions can also contain additional ingredients such as stabilizers, viscosity regulators, binders, adjuvants as well as fertilizers or other active ingredients in order to obtain special effects.

Combinations with Drought Tolerance Inducers

The compositions disclosed herein can be used in combination with other drought tolerance agents such as transgenes that induces drought tolerance.

Seed Treatments

Seed treatments include application of a pesticidal composition, optionally in combination with other bioactive, antagonistic or symbiotic agents to the surface of a seed prior to sowing. Pesticidal toxins, proteins, and/or compounds disclosed herein can be applied to seeds as dry powders, slurried powders or sprayed on the seed before planting.

The compositions disclosed herein can be formulated for seed treatments in any of the following modes: dry powder, water slurriable powder, liquid solution, flowable concentrate or emulsion, emulsion, microcapsules, gel, or water dispersible granules.

In the case of a dry powder, the active ingredient is formulated similarly to a wettable powder, but with the addition of a sticking agent, such as mineral oil, instead of a wetting agent. For example, one kg of purified talc powder (sterilized for 12 h), 15 g calcium carbonate, and 10 g carboxymethyl cellulose are mixed under aseptic conditions following the method described by Nandakumar et al (2001). Active ingredient(s) is/are mixed in a 1:2.5 ratio (suspension to dry mix) and the product is shade dried to reduce moisture content to 20-35%.

The compositions disclosed herein can also be used in combination with seed-coating agents. Such seed coating agents include, but are not limited to, ethylene glycol, polyethylene glycol, chitosan, carboxymethyl chitosan, peat moss, resins and waxes or chemical fungicides or bactericides with either single site, multisite or unknown mode of action.

In additional embodiments, the disclosed compositions can be applied to seeds by seed imbibition or as a powdered inoculum.

Seed coating methods and compositions that are known in the art can be particularly useful when they are modified by the addition of one of the embodiments of the present disclosure. Such coating methods and apparatus for their application are disclosed in, for example, U.S. Pat. Nos. 5,918,413; 5,554,445; 5,389,399; 4,759,945; and 4,465,017. Seed coating compositions are disclosed, for example, in U.S. patent application Ser. No. 05/201,00154299, U.S. Pat. Nos. 5,939,356; 5,876,739; 5,849,320; 5,791,084, 5,661, 103; 5,580,544, 5,328,942; 4,735,015; 4,634,587; 4,372, 080, 4,339,456; and 4,245,432, among others.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the coating layer.

The seed coating formulations of the present invention may be applied to the seeds using a variety of techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are known in the art.

EXAMPLES

The composition and methods set forth above will be further illustrated in the following, non-limiting Examples. The examples are illustrative of various embodiments only and do not limit the claimed invention regarding the materials, conditions, weight ratios, process parameters and the like recited herein.

Example 1: Isolation and Identification of the Microbes

*Bacillus megaterium* strain H491 was isolated from soil collected in Kwadaso, Ghana, Africa. *Bacillus megaterium* strains M018 and J142 were recovered from soils collected in California. The bacteria were recovered from the sample by traditional plate dilution methods as described by Lorch et al., 1995. Briefly, the sample was resuspended in sterile deionized water. Serial dilutions of the resuspended sample were prepared in sterile water. Some of these dilutions were spread onto agar plates (for example Potato Dextrose Agar) and incubated in the dark and at room temperature. After several days of incubation, colonies were recovered from the surface of the agar plate.

The isolates grew as dense, flat, cream colored colonies. The bacteria are gram-positive, and have no particular properties (e.g., induce drought of a plant) in its natural state.

Example 2: Drought and Salinity Tolerance of Bacillus megaterium Strain

Seeds of Tomato "Roma" were planted at the greenhouse and used at 9 days after planting. Before transplanting into cone tubes containing sunshine mix #3 media, half of the seedlings (n=18) were dipped in an MBI-508 suspension for 3.5 h, and half (n=18) were dipped in water (untreated control). One week after transplanting, the treated plants were inoculated a second time by drenching 30 mL of MBI-508 inoculum (Whole Cell Broth) in each cone; untreated controls were drenched with 30 mL of distilled water.

Drought conditions were generated by reducing the watering regime to 50% of optimal moisture necessary. This was determined to be 30 mL two times a week in. Drought treated plants were irrigated once a week (30 mL) with distilled water. The drought conditions were started immediately after the last drench and held during 6 weeks. Fresh and dry shoot weights were measured at the end of 6 weeks of drought. Results are shown

TABLE 1

| DROUGHT Fresh vegetative weight (g) | | | |
|---|---|---|---|
| H2O | | MBI 303 | |
| AVG | SD | AVG | SD |
| 1.03 | 0.17 | 6.63 | 1.77 |

TABLE 2

| SALINITY Fresh vegetative weight (g) | | | |
|---|---|---|---|
| H2O | | MBI 303 | |
| AVG | SD | AVG | SD |
| 1.71 | 0.41 | 5.14 | 1.50 |

DEPOSIT OF BIOLOGICAL MATERIAL

The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Date of Deposit |
|---|---|---|
| Bacillus megaterium strain H491 | NRRL B-50769 | Aug. $3^{rd}$, 2012 |
| Bacillus megaterium strain M018 | NRRL B-50770 | Aug. $3^{rd}$, 2012 |
| Bacillus megaterium strain J142 | NRRL B-50771 | Aug. $3^{rd}$, 2012 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.
Methods of Production As noted above, compounds or metabolites may be obtained, are obtainable or are derived from an organism having the identifying characteristics of a B. megaterium, or alternatively from any other microorganism. The methods comprise growing these organisms (e.g., in culture) and obtaining the compounds and/or compositions of the present invention by isolating these compounds from the culture of these organisms.

In particular, the organisms are cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium
Compositions Compositions may comprise whole broth cultures, liquid cultures, or suspensions of a strain from a B. megaterium, as well as supernatants, filtrates or extracts obtained from a strain of a B. megaterium, or the supernatant, filtrate and/or extract or one or more metabolites or isolated compounds derived from a strain of a B. megaterium or combinations of the foregoing which in particular have nematicidal activity against any of the following: seed gall nematodes (Afrina wevelli), bentgrass nematodes (Anguina agrostis), shoot gall nematodes (Anguina spp.), seed gall nematodes (Anguina spp., A. amsinckiae, A. balsamophila; A. tritici), fescue leaf gall nematodes (A. graminis), ear-cockle (or wheat gall) nematodes (Anguina tritici), bud and leaf (or foliar) nematodes (Aphelenchoides spp., A. subtenuis), begonia leaf (or fern, or spring crimp, or strawberry foliar, or strawberry nematodes, or summer dwarf) nematodes (A. fragariae), fern nematodes (A. olesistus), rice nematodes (A. oryzae), currant nematodes (*A. ribes*), black currant (or *chrysanthemum*) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerae, Atalodera ucri*), spine nematodes (*Bakernema variabile*), sting nematodes (*Belonolaimus* spp., *B. gracilis, B. longicaudatus*), pine wood nematodes (*Bursaphalenchus* spp., *B. xylophilus. B. mucronatus*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stem and bulb nematodes (*Ditylenchus* spp., *D. angustus. D. dipsaci, D. destructor, D. intermedius*), Mushroom spawn nematodes (*D. myceliophagus*), awl nematodes (*Dolichodorus* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiesis*), tobacco cyst nematodes (*G. rabacum*), Osborne's cyst nematodes (*G. rabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus, H. digonicus, H. dihystera, H. erythrinae, H. multicinctus, H. paragirus, H. pseudorobustus, H. solani, H. spicaudatus*), sheathoid nematodes (*Hemicriconemoides* spp., *H. biformis, H. californianus, H. chitwoodi, H. floridensis, H. wessoni*), sheath nematodes (*Hemicycliophora* spp., *H. arenaria, H. biosphaera, H. mnegalodiscus, H. parvana, H. poranga, H. sheri, H. similis, H. striatula*), cyst nematodes (*Heterodera* spp.), almond cyst nematodes (*H. amiygdali*), oat (or cereal) cyst nematodes (*H. avenae*), Cajanus (*or pigeon pea*) cyst nematodes (*H. cajani*), bermudagrass (or heart-shaped, or Valentine) cyst nematodes (*H. cardiolata*), carrot cyst nematodes (*H. carotae*), cabbage cyst nematodes or brassica root eelworm (*H. cruciferae*), nutgrass (or sedge) cyst nematodes (*H. cyperi*), Japanese cyst nematodes (*H. elachista*), fig (or ficus, or rubber) cyst nematodes (*H. fici*), galeopsis cyst nematodes (*H. galeopsidis*), soybean cyst nematodes (*H. glycines*), alfalfa root (*or pea cyst*) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), rumex cyst nemtodes (*H. rumicis*), sugar beet cyst nematodes (*H. schachtii*), willow cyst nematodes (*H. salixophila*), knawel cyst nematodes (*H. scleranrhii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli, H. caudacrena, H. gracilis, H. oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus, L. sylphus*), ring nematodes (*Macroposthonia* (=*Mesocriconema*) *xenoplax*), cystoid nematodes (*Meloidodera* spp.), pine cystoid nematodes (*M. floridensis*), tadzhik cystoid nematodes (*M. radshikistanica*), cystoid body nematodes (*Meloidoderita* spp.), stunt nematodes (*Merlinius* spp., *M. brevidens, M. conicus, A. grandis, M. microdorus*), root-knot nematodes (*Meloidogyne* spp., *M. acronea, M. arenaria, M. artiellia, M. brevicauda, M. camelliae, M. carolinensis, M. chirwoodi, M. exigua, M. graminicola, M. hapla, M. hispanica, M. incognita, M. incognita acrita, M. indica, M. inornata, M. javanica, M. kikuyuensis, M. konaensis, M. mali, M. microtyla, M. naasi, M. ovalis, M. platani, M. querciana, M. sasseri, M. tadshikistanica, M. thamesi*), knapweed nematodes (*Mesoanguina picridis*), Douglas fir nematodes (*Nacobbodera chitwoodi*), false root-knot nematodes (*Nacobbus aberrans, N. batatiformis, N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius, P. minor, P. porosus, P. renifer*), pin nematodes (*Paratylenchus* spp., *P. baldaccii, P. bukowinensis, P. curviratus, P. dianthus, P. elachistus, P. hamatus, P. holdemani, P. italiensis, P. lepidus, P. nanus, P. neoamplycephlus, P. similis*), lesion (or meadow) nematodes (*Pratylenchus* spp., *P. alleni, P. brachyurus, P. coffeae, P. convallariae. P. crenatus, P. flakkensis, P. goodeyi, P. hexincisus, P. leiocephalus, P. minyus, P. musicola, P. neglectus, P. penetrans, P. pratensis, P. scribneri, P. thornei, P. vulnus, P. zeae*), stem gall nematodes (*Prerotylenchus cecidogenus*), grass cyst nematodes (*Punctodera punctate*), stunt nematodes (*Quinisulcius acutus, Q. capitatus*), burrowing nematodes (*Radopholus* spp.), banana-root nematodes (*R. similis*), rice-root nematodes (*R. ortzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), *Sarisodera hydrophylla*, spiral nematodes (*Scutellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecavermicularus andinus*), stubby-root nematodes (*Trichodorus* spp., *T. christiei, T. kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T. ebriensis, T. elegans, T. golden, T. graciliformis, T. martini, T. mashhoodi, T. microconus, T. nudus, T. oleraceae, T. penniseti, T. punensis*), citrus nematodes (*Tylenchulus semipenetrans*), dagger nematodes (*Xiphinema* spp., *X. americanum, X. bakeri, X. brasiliense, X. brevicolle, X. chambersi, X. coxi, X. diversicaudatum X. index, X. insigne, X. nigeriense, X. radicicola, X. setariae, X. vulgarae, X. vuittenezi*).

The compositions set forth above can be formulated in any manner. Non-limiting formulation examples include but are not limited to Emulsifiable concentrates (EC), Wettable powders (WP), Soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), etc. In any formulation described herein, percent of the active ingredient is within a range of 0.01% to 99.99%.

The compositions may be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower.

A composition may comprise gel-encapsulated active ingredient(s). Such gel-encapsulated materials can be prepared by mixing a gel-forming agent (e.g., gelatin, cellulose, or lignin) with a culture or suspension of live or inactivated *B. megaterium*, or a cell-free filtrate or cell fraction of a *B. megaterium* culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may be combined with another microorganism and/or pesticide (e.g. nematicide, fungicide, insecticide). The microorganism may include but is not limited to an agent derived from *Bacillus* sp. (e.g., *Bacillus firmus, Bacillus thuringiensis, Bacillus pumilus, Bacillus licheniformis, Bacillus amyloliquefaciens, Bacillus subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp (*S. bikiniensis, S. costaricanus, S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplrnium, Neobulgaria, Daldinia, Aspergillus, Chaetomium, Lysobacter* spp, *Lachnum papyraceum, Verticillium suchlasporium, Arthrobotrys oligospora, Verticillium chlamydosporium, Hirsutella rhossiliensis, Pochonia chlamydosporia, Pleurotus ostreatus, Omphalotus olearius, Lampteromyces japonicas, Brevudimonas* sp., *Muscodor* sp.

Alternatively, the agent may be a natural oil or oil-product having nematicidal, fungicidal and/or insecticidal activity (e.g., paraffinic oil, tea tree oil, lemongrass oil, clove oil, cinnamon oil, citrus oil including but not limited to bitter orange, orange, lemon; rosemary oil, pyrethrum, allspice, bergamot, blue gum, camomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, saponins). Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a *Reynoutria* extract.

The fungicide can also be a multi-site non-inorganic, chemical fungicide selected from the group consisting of chloronitrile, quinoxaline, sulphamide, phosphonate, phosphite, dithiocarbamate, chloralkythios, phenylpyridinamine, cyano-acetamide oxime.

As noted above, the composition may further comprise a nematicide. This nematicide may include but is not limited to chemicals such as organophosphates, carbamates, and fumigants, and microbial products such as avermectin, *Myrothecium* sp. Biome (*Bacillus firmus*), *Pasteuria* spp., *Paecilomyces*, and organic products such as saponins and plant oils.

The compositions may be applied using methods known in the art. Specifically, these compositions may be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment of the plants and plant parts with the compositions set forth above may be carried out directly or by allowing the compositions to act on their surroundings, habitat or storage space by, for example, immersion, spraying, evaporation, fogging, scattering, painting on, injecting. In the case that the composition is applied to a seed, the composition may be applied to the seed as one or more coats prior to planting the seed, or applied as a slurry or dust when planting, using one or more coats using methods known in the art. The seed in a particular embodiment may be a genetically modified seed.

Plants that may be treated include but are not limited to: (A) Major edible food crops, which include but are not limited to (1) Cereals (e.g., African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, sorghum, Sorghum spp., rye, spelt wheat); (2) Fruits (e.g., abiu, acerola, achacha, African mangosteen, alpine currant, ambarella, American gooseberry, American persimmon, apple, apricot, arazi, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blue-berried honeysuckle, borojí, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee *Arabica*, coffee *robusta*, Costa Rica pitahaya, currants, custard apple, date, date-plum, dog rose, dragonfruit, durian, elderberry, elephant apple, Ethiopian eggplant, European nettle tree, European wild apple, feijoa, fig, gac, genipapo, giant granadilla, gooseberry, goumi, grape, grapefruit, great morinda, greengage, guava, hardy kiwi, hog plum, horned melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain papaya, mountain soursop, mulberry, naranjilla, natal plum, northern highbush blueberry, olive, otaheite gooseberry, oval kumquat, papaya, para guava, passionfruit, pawpaw, peach, peach-palm, pear, pepino, pineapple, pitomba *Eugenia luschnathiana*, pitomba *Talisia esculenta*, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L. chinense*), yellow mombin, yellow pitaya, yellow-fruited strawberry, guava, (3) Vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, barbados gooseberry, beet, beet root, bitter gourd, bitter vetch, bitterleaf, black mustard, black radish, black salsify, blanched celery, breadfruit, broad bean, broccoli, brussels sprout, Buck's horn plantain, buttercup squash, butternut squash, cabbage, caigua, calabash, caraway seeds, carob, carrot, cassabanana, cassava, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, good king henry, grass pea, groundnut, guar bean, horse gram, horseradish, hyacinth bean, iceplant, Indian fig, Indian spinach, ivy gourd, Jerusalem artichoke, jicama, jute, kale, kohlrabi, konjac, kurrat, leek, lentil, lettuce, Lima bean, lotus, luffa, maca, maize, mangel-wurzel, mashua, moso bamboo, moth bean, mung bean, napa cabbage, neem, oca, okra, oldham's bamboo, olive, onion, parsnip, pea, pigeon pea, plantain, pointed gourd, potato, pumpkins, squashes, quinoa, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop *trapa bicornis*, water caltrop *trapa natans*, water morning slory, watercress, welsh onion, west African okra, west Indian gherkin, white goosefoot, white yam, winged bean, winter purslane, yacón, yam, yard-long bean, zucchinietables); (4) Food crops (e.g., abiu, acerola, achacha, ackee, African mangosteen, African rice, agate, air potato, alpine currant, *Amaranthus* app., Ambarrella, American gooseberry, American groundnut, American persimmon, antroewa, apple, apricot, arazA, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, betel nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blueberried honeysuckle, borojö, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassava, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (*Arabica* and *Robusta* types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, durum wheat, eddoe, eggplant, einkorn wheat, elderberry, elephant apple, elephant foot yam, elephant garlic, emmer wheat, endive, enset, Ethiopian eggplant, European nettle tree, European wild apple, feijoa, fig, finger millet, florence fennel, fluted gourd, foxtail millet, gac, garden rocket, garlic, genipapo, geocarpa groundut, giant granadilla, good king henry, gooseberry, goumi, grape, grapefruit, grass pea, great *morinda*, greengage, groundnut, grumichama, guar bean, guava, hairy crabgrass, hardy kiwi, hog plum, horned melon, horse gram, horse mango, horseradish, hyacinth bean, iceplant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, luffa, lychee, maca, maize, malay apple, mamey saptoe, mammee apple, mangel-wurzel, mango, mangosteen, maprang, marang, mashua, medlar, melon, Mirabelle plum, miracle fruit, monk fruit, monkey jack, moriche palm, moso bamboo, moth bean, mountain papaya, mountain soursop, mulberry, mung bean, mushrooms, nance, napa cabbage, naranjilla, natal plum, neem, northern highbush blueberry, oat, oca, oil palm, okra, oldman's bamboo, olive, onion, orange, otaheite gooseberry, oval kumquat, papaya, para guava, parsnip, passionfruit, pawpaw, pea, peach, peach-palm, pear, pearl millet, pepino, pigeon pea, pineapple, Pitomba (*Eugenia luschnathiana, Talisia esculenta*), plantain, plum, pointed gourd, pomegranate, pomelo, potato, proso millet, pulasan, pumpkins and squashes, purple chokeberry, quince, quinoa, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, sorghum, Sorghum spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, tef, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacón, yam, yangmei, yard-long bean, yellow mombin, yellow pitaya, yellow-fruited strawberry guava, zucchini; (B) Other edible crops, which includes but is not limited to (1) Herbs (e.g., *Absinthium*, alexanders, basil, bay laurel, betel nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, ginseng, gray santolina, herb hyssop, holy basil, hop, jasmine, kaffir lime, lavender, lemon balm, lemon basil, lemon grass, lovage, marjoram, mint, oregano, parsley, peppermint, perilla, pot marigold, rooibos, rosemary, sage, shiny-leaft buckthorn, sorrel, spearmint, summer savory, tarragon, Thai basil, valerian, watercress, wild betel, winter savory, yerba mate); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard); (2) Medicinal plants (e.g., *absinthium*, alfalfa, aloe vera, anise, artichoke, basil, bay laurel, betel leaf, betel nut, bilberry, black cardamom, black mustard, black pepper, blue gum, borojó, camomlie, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray santolina, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red acacia, red currant, rooibos, safflower, sage, shiny-leaf buckthorn, sorrel, spilanthes, star anise, tarragon, tea, turmeric, valerian, velvet bean, watercress, white mustard, white sapote, wild betel, wolfberry (*Lycium barbarum, L. chinense*), yerba mate); (3) Stimulants (e.g., betel leaf, betel nut, cacao, chili pepper (*Capsicum annuum, C. baccatum, C. chinense, C. frutescens, C. pubescens*), chili peppers, coffee, coffee (*Arabica, Robusta*), cola nut, khat, Liberian coffee, tea, tobacco, wild betel, yerba mate); (4) Nuts (e.g., almond, betel nut, Brazil nut, cashew nut, chestnut, Chinese water chestnut, coconut, cola nut, common walnut, groundnut, hazelnut, Japanese stone oak, macadamia, nutmeg, paradise nut, pecan nut, pistachio nut, walnut); (5) Edible seeds (e.g., black pepper, Brazil nut, chilacayote, cola nut, fluted gourd, lotus, opium, quinoa, sesame, sunflower, water caltrop (*Trapa bicornis, T. natans*); (6) Vegetable oils (e.g., black mustard, camelina, castor bean, coconut, cotton, linseed, maize, neem, niger seed, oil palm, olive, opium, rapeseed, safflower, sesame, soybean, sunflower, tung tree, turnip); (7) Sugar crops (e.g., Asian palmyra palm, silver date palm, sorghum, sugar beet, sugarcane); (8) Pseudocereals (e.g., *Amaranthus* spp., buckwheat, quinoa, red amaranth); (9) Aphrodisiacs (e.g., borojó, celery, durian, garden rocket, ginseng, maca, red acacia, velvet bean); (C) Non food categories, including but not limited to (1) forage and dodder crops (e.g., agate, alfalfa, beet, broad bean, camelina, catjang, grass pea, guar bean, horse gram, Indian barnyard millet, Japanese barnyard millet, lespedeza, lupine, maize, mangel-wurzel, mulberry, niger seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassava, maize, rapeseed, sorghum, soybean, Sudan grass, sugar beet, sugarcane, wheat); (4) Alcohol production, (e.g., barley, plum, potato, sugarcane, wheat, sorghum); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray santolina, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, sunn hemp, trefoil, velvet bean, vetch); (7) Erosion prevention (e.g., bamboo, cocoplum; (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, chrysanthemum, daffodil, dahlia, freesia, gerbera, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, chrysanthemum, cocoplum, common lavender, crocus, daffodil, dahlia, freesia, gerbera, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia, almond, apple, apricot, arborvitae nigra american, arborvitae, ash, aspen, azalea, baldcypress, beautybush, beech, bijch, black tupelo, blackberry, blueberry, boxwood, buckeye, butterfly bush, butternut, camellia, catalpa, cedar, cherry, chestnut, coffeetree, crab trees, crabapple, crapemyrtle, cypress, dogwood, douglasfir, ebony, elder American, elm, fir, forsythia, ginkgo, goldenraintree, hackberry, hawthorn, hazelnut, hemlock, hickory, holly, honeylocust, horsechestnut, hydrangea, juniper, lilac, linden, magnolia, maple, mockorange, mountainash, oak, olive, peach, pear, pecan, pine, pistache, planetree, plum, poplar, pivet, raspberry, redbud, redcedar, redwood, rhododendron, rose-of-sharon, sassafras, sequoia, serviceberry, smoketree, soapberry, sourwood, spruce, strawberry tree, sweetshrub, sycamore, tuliptree, viburnum, walnut, weigela, willow, winterberry, witchhazel, zelkova; (E) Turf which includes but is not limited to Kentucky bluegrass, tall fescue, Bermuda grass, zoysia grass, perennial ryegrass, fine fescues (e.g.; creeping red, chewings, hard, or sheep fescue).

The compositions may also be applied to the soil using methods known in the art (see, for example, Chitwood, "Nematicides", available at naldc.nal.usda.gov/download/43874/PDF. Such methods include but are not limited to fumigation, drip irrigation or chemigation, soil incorporation, soil drenching, seed treatment and dressing, bare root dip.

Pesticidal Uses

The compositions, cultures, supernatants, metabolites and pesticidal compounds set forth above may be used as pesticides. In particular, the compositions, cultures, supernatants, metabolites and pesticidal compounds as set forth above may be used as insecticides and nematicides, alone or in combination with one or more pesticidal substances set forth above. Specifically, nematodes that may be controlled using the method set forth above include but are not limited to free living nematodes, parasitic nematodes such as root-knot, cyst, and lesion nematodes, including but not limited to seed gall nematodes (*Afrina wevelli*), bentgrass nematodes (*Anguina agrostis*), shoot gall nematodes (*Anguina* spp.), seed gall nematodes (*Anguina* spp., *A. amsinckiae*, *A. balsamophila*; *A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerae*, *Atalodera ucri*), spine nematodes (*Bakernema variabile*), sting nematodes (*Belonolaimus* spp., *B. gracilis*, *B. longicaudatus*), pine wood nematodes (*Bursaphalenchus* spp., *B. xylophilus*, *B. mucronatus*), sessile nematodes (*Cacopaurus* spp., *C. epacris*, *C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae*, *C. decalineatum*, *C. spinalineatum*). ring nematodes (*Criconemella axeste*, *C. curvata*, *C. macrodora*, *C. parva*), ring nematodes (*Criconenaides* spp., *C. citri*, *C. simile*), spine nematodes (*Crossonema fimbriatum*), eucalypt cystoid nematodes (*Cryphodera eucalypti*), bud, stem and bulb nematodes (*Ditylenchus* spp., *D. angustus*, *D. dipsaci*, *D. destructor*, *D. intermedius*), Mushroom spawn nematodes (*D. myceliophagus*), awl nematodes (*Dolichodorus* spp., *D. heterocephalus*, *D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus*, *H. digonicus*, *H. dihystera*, *H. erythrinae*, *H. multicinctus*, *H. paragirus*, *H. pseudorobustus*, *H. solani*, *H. spicaudatus*), sheathoid nematodes (*Hemicriconemoides* spp., *H. biformis*, *H. californianus*, *H. chitwoodi*, *H. floridensis*, *H. wessoni*), sheath nematodes (*Hermicyliophora* spp., *H. arenaria*, *H. biosphaera*, *H. megalodiscus*, *H. parvana*, *H. poranga*, *H. sheri*, *H. similis*, *H. striatula*), cyst nematodes (*Heterodera* spp.), almond cyst nematodes (*H. amygdali*), oat (or cereal) cyst nematodes (*H. avenae*). Cajanus (or pigeon pea) cyst nematodes (*H. cajani*), bermudagrass (or heart-shaped, or Valentine) cyst nematodes (*H. cardiolata*), carrot cyst nematodes (*H. carotae*), cabbage cyst nematodes or *brassica* root eelworm (*H. cruciferae*), nutgrass (or sedge) cyst nematodes (*H. cyperi*), Japanese cyst nematodes (*H. elachista*), fig (or ficus, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*). lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), *rumex* cyst nemtodes (*H. rumicis*), sugar beet cyst nematodes (*H. scleranthii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli*, *H. caudacrena*, *H. gracilis*, *H. oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Langidorus* spp., *L. africanus*, *L. sylphus*), ring nematodes (*Macroposthonia* (=*Mesocriconema*) *xenoplax*), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens*, *M. conicus*, *M. grandis*, *M. microdorus*), root-knot nematodes (*Meloidogyne* spp., *M. acronea*, *M. arenaria*, *M. artiellia*, *M. brevicauda*, *M. camelliae*, *M. carolinensis*, *M. chitwoodi*, *M. exigua*, *M. graminicola*, *M. hapla*, *M. hispanica*, *M. incognita*, *M. incognita acrita*, *M. indica*, *M. inornata*, *M. javanica*, *M. kikuyuensis*, *M. konaensis*, *M. mali*, *M. microtyla*, *M. naasi*. *M. ovalis*, *M. platani*, *M. querciana*, *M. sasseri*, *M. tadshikistanica*, *M. thamesi*), knapweed nematodes (*Mesoanguina picridis*), Douglas fir nematodes (*Nacobbodera chitwoodi*), false root-knot nematodes (*Nacobbus aberrans*, *N. baratiformis*, *N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius*, *P. minor*, *P. porosus*, *P. renifer*), pin nematodes (*Paratylenchus* spp., *P. baldaccii*, *P. bukowinensis*, *P. cur-

*vitatus, P. dianthus, P. elachistus, P. hamatus, P. holdemani, P. italiensis, P. lepidus, P. nanus, P. neoamplycephalus, P. similis*), lesion (or meadow) nematodes (*Pratylenchus* spp., *P. alleni, P. brachyurus, P. coffeae, P. convallariae, P. crenatus, P. flakkensis, P. goodeyi, P. hexincisus, P. leiocephalus, P. minyus, P. musicola, P. neglectus, P. penetrans, P. pratensis, P. scribneri, P. thornei, P. vulnus, P. zeae*), stem gall nematodes (*Pterotylenchus cecidogenus*), grass cyst nematodes (*Punctodera punctate*). stunt nematodes (*Quinisulcius acutus, Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), *Sarisodera hydrophylla*, spiral nematodes (*Scutellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecavermiculatus andinus*), stubby-root nematodes (*Trichodorus* spp., *T. christiei, T. kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T. ebriensis, T. elegans, T. golden, T. graciliformis, T. martini, T. mashhoodi, T. microconus, T. nudus, T. oleraceae, T. penniseri, T. punensis*), citrus nematodes (*Tylenchulus semipenetrans*), dagger nematodes (*Xiphinema* spp., *X. americanum, X. bakeri, X. brasiliense, X. brevicolle, X. chambersi, X. coxi, X. diversicaudatum X. index, X. insigne, X. nigeriense, X. radicicola, X. setariae, X. vulgarae, X. vuittenezi*).

Application of an effective pesticidal control amount of a supernatant, filtrate or extract containing a pesticidally active metabolite, or isolated compound produced by the *B. megaterium* or application of combinations of the foregoing is provided. The strain or supernatant or filtrate or extract, metabolite and/or compound is applied, alone or in combination with another pesticidal substance, in an effective pest control or pesticidal amount. An effective amount is defined as that quantity of microorganism cells, supernatant, filtrate or extract, metabolite and/or compound alone or in combination with another pesticidal substance that is sufficient to modulate pest infestation. The effective rate can be affected by pest species present, stage of pest growth, pest population density, and environmental factors such as temperature, wind velocity, rain, time of day and seasonality. The amount that will be within an effective range in a particular instance can be determined by laboratory or field tests.

Plant Growth Promotion

The compositions disclosed herein, in particular, *Bacillus megaterium* and/or a supernatant, filtrate, extract, compound, metabolite or cell fraction obtained from a culture of *B. megaterium*, can be used to modulate or more particularly promote growth of plants, e.g. crops such as fruit (e.g., strawberry), vegetable (e.g., tomato, squash, pepper, eggplant), or grain crops (e.g., soy, wheat, rice, corn), tree, flower, ornamental plants, shrubs (e.g., cotton, roses), bulb plant (e.g., onion, garlic) or vine (e.g., grape vine). The compositions can also be used to modulate the germination of a seed(s) in a plant(s).

The compositions disclosed herein, or formulated product, can be used alone or in combination with one or more other components as described below, such as growth promoting agents and/or anti-phytopathogenic agents in a tank mix or in a program (sequential application called rotation) with predetermined order and application interval during the growing season. When used in a combination with the above-mentioned products, at a concentration lower than recommended on the product label, the combined efficacy of the two or more products (one of which is the said composition disclosed herein) is, in certain embodiments, greater than the sum of each individual component's effect. Hence, the effect is enhanced by synergism between these two (or more) products, and the risk for the development of pesticide resistance among the plant pathogenic strains is reduced.

The composition can be applied by root dip at transplanting, specifically by treating a fruit or vegetable with the composition by dipping roots of the fruit or vegetable in a suspension of said composition (about 0.25 to about 1.5% and more particularly about 0.5% to about 1.0% by volume) prior to transplanting the fruit or vegetable into the soil.

Alternatively, the composition can be applied by drip or other irrigation system.

Specifically, the composition can be injected into a drip irrigation system. In a particular embodiment, the composition is applied at a concentration of $1 \times 10^8$ CFU/ml in a volume of approximately 11 to approximately 4 quarts per acre.

In yet another embodiment, the composition can be added as an in-furrow application. Specifically, the composition can be added as an in-furrow spray at planting using nozzles calibrated to deliver a total output of 2-6 gallons/acre. Nozzles are placed in the furrow opener on the planter so that the pesticide application and seed drop into the furrow are simultaneous.

Mixtures of the disclosed compositions with, for example, a solid or liquid adjuvant are prepared in known manner. For example, mixtures can be prepared by homogeneously mixing and/or grinding the active ingredients with extenders such as solvents, solid carriers and, where appropriate, surface-active compounds (surfactants). The compositions can also contain additional ingredients such as stabilizers, viscosity regulators, binders, adjuvants as well as fertilizers or other active ingredients in order to obtain special effects.

Combinations with Plant Growth Promoting Agents

The compositions disclosed herein can be used in combination with other growth promoting agents such as synthetic or organic fertilizers (e.g., di-ammonium phosphate, in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and growth promoting microbes, such as, for example, *Bacillus* spp., *Pseudomonads, Rhizobia*, and *Trichoderma*.

Seed Treatments

Seed treatments include application of a pesticidal composition, optionally in combination with other bioactive, antagonistic or symbiotic agents to the surface of a seed prior to sowing. Pesticidal toxins, proteins, and/or compounds disclosed herein can be applied to seeds as dry powders, slurried powders or sprayed on the seed before planting.

The compositions disclosed herein can be formulated for seed treatments in any of the following modes: dry powder, water slurriable powder, liquid solution, flowable concentrate or emulsion, emulsion, microcapsules, gel, or water dispersible granules.

In the case of a dry powder, the active ingredient is formulated similarly to a wettable powder, but with the addition of a sticking agent, such as mineral oil, instead of a wetting agent. For example, one kg of purified talc powder (sterilized for 12 h), 15 g calcium carbonate, and 10 g carboxymethyl cellulose are mixed under aseptic conditions following the method described by Nandakumar et al (2001). Active ingredient(s) is/are mixed in a 1:2.5 ratio (suspension to dry mix) and the product is shade dried to reduce moisture content to 20-35%.

The compositions disclosed herein can also be used in combination with seed-coating agents. Such seed coating agents include, but are not limited to, ethylene glycol, polyethylene glycol, chitosan, carboxymethyl chitosan, peat moss, resins and waxes or chemical fungicides or bactericides with either single site, multisite or unknown mode of action.

In additional embodiments, the disclosed compositions can be applied to seeds by seed imbibition or as a powdered inoculum.

Anti-Phytopathogenic Agents

The compositions disclosed herein can also be used in combination with other anti-phytopathogenic agents, such as plant extracts, biopesticides, inorganic crop protectants (such as copper), surfactants (such as rhamnolipids; Gandhi et al., 2007) or natural oils such as paraffinic oil and tea tree oil possessing pesticidal properties or chemical fungicides or bactericides with either single site, multisite or unknown mode of action. As defined herein, an "anti-phytopathogenic agent" is an agent that modulates the growth of a plant pathogen, particularly a pathogen causing soil-borne disease on a plant, or alternatively prevents infection of a plant by a plant pathogen. A plant pathogen includes but is not limited to a fungus, bacteria, actinomycete or virus.

As noted above, the anti-phytopathogenic agent can be a single-site anti-fungal agent which can include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine). In a more particular embodiment, the antifungal agent is a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole). In a most particular embodiment, the antifungal agent is myclobutanil. In yet another particular embodiment, the antifungal agent is a quinone outside inhibitor (e.g., strobilurin). The strobilurin may include but is not limited to azoxystrobin, kresoxim-methyl or trifloxystrobin. In yet another particular embodiment, the anti-fungal agent is a quinone, e.g., quinoxyfen (5,7-dichloro-4-quinolyl 4-fluorophenyl ether).

In yet a further embodiment, the fungicide is a multi-site non-inorganic, chemical fungicide selected from the group consisting of chloronitrile, quinoxaline, sulphamide, phosphonate, phosphite, dithiocarbamate, chloralkythios, phenylpyridine-amine, and cyano-acetamide oxime.

In yet a further embodiment, the anti-phytopathogenic agent can be streptomycin, tetracycline, oxytetracycline, copper, or kasugamycin.

Example 3: Biochemical Characterization of *B. megaterium* H491

*Bacillus megaterium* strain H491 was determined to be gram positive, urease positive, catalase positive, oxidase negative and lipase positive. Extensive biochemical characterization of the isolate was performed using Biolog Phenotypic Microarrays. The full Biolog Phenotypic microarray consists of twenty 96-well plates, each well containing a different carbon, nitrogen, phosphorus or other nutrient source. Some of the plates also contain different antibiotics, metals, etc., to evaluate susceptibility of the isolate. Absorbance readings from the wells in each plate were compared to a negative control well. Absorbance readings above the negative control threshold indicated growth of the isolate under the conditions in a particular well, while reading at or below the negative control indicated that the isolate failed to thrive under the specific conditions of that well. The test was performed for H491 at 25° C., with duplicate plates for each phenotype test.

*B. megaterium* strain H491 was able to utilize the following carbohydrates, organic acids and peptides as carbon sources: L-Arabinose, N-Acetyl-D-Glucosamine, D-Galactose, L-Aspartic acid, L-Proline, D-Trehalose, Dulcitol, Glycerol, D-Glucuronic acid, D-Gluconic acid, D-Xylose, L-Lactic acid, D-Mannitol, L-Glutamic acid, D-Glucose-6-Phosphate, D-Galactonic acid-g-Lactone, D,L-Malic acid, D-Ribose, D-Fructose, a-D-Glucose, Maltose, D-Melibiose, Thymidine, L-Asparagine, D-Aspartic acid, a-Ketoglutaric acid, Sucrose, L-Glutamine, Maltotriose, Citric acid, Fumaric acid, Bromosuccinic acid, L-Alanine, Ala-Gly, Methylpyruvate, L-Malic acid, L-Lyxose, Pyruvic acid, Dextrin, Glycogen, D-Arabinose, Arbutin, 2-Deoxy-D-Ribose, 3-O-b-D-Galactopyranosyl-D-Arabinose, Gentiobiose, Palatinose, D-Raffinose, Salicin, Stachyose, D-Tagatose, Turanose, g-Amino-N-Butyric acid, D-Glucosamine, b-Hydroxybutyric acid, 5-Keto-D-Gluconic acid, Quinic acid, D-Tartaric acid, L-Tartaric acid, L-Ornithine, L-Pyroglutamic acid, and Dihydroxyacetone.

The following substrates were not utilized as carbon sources, as evidenced by absorbance readings below the negative control threshold: D-Saccharic acid, D-Serine, D-Sorbitol, L-Fucose, D,L-a-Glycerol Phosphate, L-Rhamnose, D-Glucosaminic acid, 1,2-Propanediol, a-Ketobutyric acid, a-D-Lactose, D-Glucose-1-Phosphate, a-Hydroxyglutaric acid-g-Lactone, a-Hydroxybutyric acid, Adonitol, 2'-Deoxyadenosine, Adenosine, D-Threonine, Propionic acid, Mucic acid, Glycolic acid, Tricarballylic acid, L-Threonine, N-Acetyl-D-Mannosamine, D-Malic acid, Gly-Pro, L-Galactonic acid-g-Lactone, Chondroitin Sulfate C, a-Cyclodextrin, Inulin, Laminarin, Mannan, N-Acetyl-D-Galactosamine, N-Acetyl-Neuraminic acid, b-D-Allose, Amygdalin, D-Arabitol, L-Arabitol, i-Erythritol, D-Fucose, L-Glucose, D-Lactitol, b-Methyl-D-Galactoside, 3-Methylglucose, b-Methyl-D-Glucuronic acid, a-Methyl-D-Mannoside, Sedoheptulosan, L-Sorbose, Xylitol, N-Acetyl-D-Glucosaminitol, d-Amino Valeric acid, Capric acid, Caproic acid, Citraconic acid, Citramalic acid, 2-Hydroxybenzoic acid, 4-Hydroxybenzoic acid, a-Keto-Valeric acid, Itaconic acid, D-Lactic acid Methyl Ester, Malonic acid, Melibionic acid, Oxalic acid, D-Ribono-1,4-Lactone, Sebacic acid, Sorbic acid, Succinamic acid, Acetamide, L-Alaninamide, N-Acetyl-L-Glutamic acid, Glycine, L-Homoserine, Hydroxy-L-Proline, L-Isoleucine, L-Leucine, L-Lysine, L-Phenylalanine, L-Valine, D,L-Carnitine, sec-Butylamine, D,L-Octopamine, 2,3-Butanediol, 2,3-Butanedione, and 3-Hydroxy-2-butanone.

H491 was able to utilize the following amino acids as nitrogen sources: L-Glutamine, L-Pyroglutamic acid, L-Glutamic acid, L-Asparagine, L-Ornithine, D-Asparagine, L-Proline, L-Aspartic acid, D-Alanine, L-Arginine, L-Alanine, L-Serine, D-Aspartic acid, L-Tryptophan, and L-Tyrosine. It was also able to utilize Urea, Putrescine, Agmatine, N-Acetyl-D-Glucosamine, Cytidine, Guanosine, Inosine, Xanthine, Uric acid, Allantoin, g-Amino-N-Butyric acid and a-Amino-N-Valeric acid as additional organic nitrogen sources. H491 could also utilize ammonia, nitrite and nitrate as inorganic nitrogen sources.

H491 was able to utilize a variety of substrates as phosphorous sources, including Phosphate, Thiophosphate, Dithiophosphate, D-Glucosamine-6-Phosphate, Cysteamine-S-Phosphate, Uridine 2',3'-Cyclic Monophosphate, and Thymidine 5'-Monophosphate.

Metabolism of H491 was inhibited below pH 5, but restored at pH 4.5 in the presence of L-arginine, L-methionine and 5-hydroxy-lysine. Growth was observed between pH 5 to pH 10. The strain did not tolerate NaCl above 5%, and only slight growth was detected at 4% NaCl. The Bergey's Manual of Systematic Bacteriology indicates that *Bacillus megaterium* isolates can use citrate as a sole carbon source; most can grow at 7% NaCl, but none at 10% NaCl; and most strain do not reduce nitrate. In contrast, H491 did not tolerate NaCl above 5%, and was able to utilize both nitrate and nitrite as nitrogen sources.

Example 4: Production of *B. megaterium* H491, M018 and J142 by Fermentation A supernatant with nematicidal activity was produced through the submerged fermentation of strain H491 under aerobic conditions in liquid V8 medium. Other suitable media include tryptic soy broth, or any nutrient medium containing appropriate carbon and nitrogen sources.

A seed plate was started by streaking a fresh potato dextrose agar plate with a small amount of strain H491, using a sterile loop. The plate was incubated at 25° C. for 2-3 days or until enough biomass was evident on the surface of the plate.

A 50 mL V8 medium seed flask was inoculated with one loopful of material collected from the agar plate surface. The seed was incubated in a shaker at 200 rpm for 2 days.

A glass 2.8 L, non-baffled fernbach flask containing 500 mL of V8 medium was aseptically inoculated with 2% of seed. The fermentation was allowed to proceed at 25° C. for 5 days with constant agitation at 150-200 rpm.

The supernatant was obtained by separation the cells from the spent fermentation broth by centrifugation, or other means of separation. Activity of the supernatant was verified by means of the bioassay described below.

Example 5: Further Characterization of *B. megaterium* H491, J142 and M018

Resistance to Antibiotics

Antibiotic susceptibility of *Bacillus megaterium* strains H491, J142 and M018 was tested using antibiotic disks on Muller-Hinton medium as described in PML Microbiological's technical data sheet #535. Results obtained after 48-hour incubation at 25° C. are presented in Table 1.

TABLE 1

Susceptibility of *Bacillus megaterium* H491, J142 and M018 to various antibiotics. Susceptibility degree is indicated by +++ (very), ++ (somewhat), + (marginally), and resistance is indicated by (−).

| | Concentration (mg) | H491 | J142 | M018 |
|---|---|---|---|---|
| Tetracycline | 30 | +++ | +++ | +++ |
| Kanamycin | 30 | +++ | +++ | +++ |

TABLE 1-continued

Susceptibility of *Bacillus megaterium* H491, J142 and M018 to various antibiotics. Susceptibility degree is indicated by +++ (very), ++ (somewhat), + (marginally), and resistance is indicated by (−).

| | Concentration (mg) | H491 | J142 | M018 |
|---|---|---|---|---|
| Erythromycin | 15 | +++ | +++ | +++ |
| Streptomycin | 10 | +++ | +++ | + |
| Penicillin | 10 | +++ | − | ++ |
| Ampicillin | 10 | +++ | +++ | ++ |
| Oxytetracycline | 30 | +++ | +++ | +++ |
| Chloramphenicol | 30 | +++ | +++ | ++ |
| Ciprofloxacin | 5 | +++ | +++ | +++ |
| Gentamicin | 10 | +++ | +++ | +++ |
| Piperacillin | 100 | +++ | + | ++ |
| Cefuroxime | 30 | +++ | +++ | +++ |
| Imipenem | 10 | +++ | +++ | +++ |
| Sulphamethoxazole-Trimethoprim | 23.75/25 | +++ | +++ | +++ |

Chemical Sensitivity

Chemical sensitivity data was obtained from the Biolog Phenotypic Microarray. H491 was found to be susceptible to the following compounds: Chlortetracycline, Lincomycin, Amoxicillin, Cloxacillin, Minocycline, Capreomycin, Demeclocycline, Nafcillin, Cefazolin, Enoxacin, Nalidixic acid, Chloramphenicol, Erythromycin, Neomycin, Cephalothin, Kanamycin, Penicillin G, Tetracycline, Carbenicillin, Oxacillin, Penimepicycline, Paromomycin, Vancomycin, Sisomicin, Novobiocin, 2,4-Diamino-6,7-diisopropylpteridine, Sulfadiazine, Benzethonium Chloride, Tobramycin, Sulfathiazole, 5-Fluoroorotic acid, Sulfamethoxazole, L-Aspartic-b-hydroxamate, Spiramycin, Rifampicin, Dodecyltrimethyl ammonium bromide, Azlocillin, 2,2'-Dipyridyl, 6-Mercaptopurine monohydrate, Doxycycline, Potassium chromate, Cefuroxime, 5-Fluorouracil, Rolitetracycline, Cesium chloride, Thallium (I) acetate, Cobalt (II) chloride, Trifluoperazine, Tylosin, Acriflavine, Furaltadone, Sanguinarine chloride, Fusaric acid, Boric acid, 1-Hydroxypyridine-2-thione (pyrithione), Sodium Cyanate, Cadmium chloride, Iodoacetic acid, Sodium Dichromate, Cefoxitin, Sodium metaborate, Chloramphenicol, Sodium metavanadate, Chelerythrine chloride, Carbenicillin, Sodium Nitrite, Ethylene Glycol-bis(b-Aminoethyl ether)-N,N,N',N'-Tetraacetic Acid, Promethazine, Sodium orthovanadate, Guanidine hydrochloride, D-Cycloserine, EDTA, 5,7-Dichloro-8-hydroxyquinaldine, 5,7-Dichloro-8-hydroxyquinoline, Fusidic acid, sodium salt, 1,10-Phenanthroline Monohydrate, Phleomycin, Domiphen bromide, Alexidine, 5-Nitro-2-furaldehyde semicarbazone (Nitrofurazone), Methyl viologen, Oleandomycin, phosphate salt, Puromycin, Carbonyl-cyanide m-chlorophenylhydrazone (CCCP), Sodium Azide, Menadione, sodium bisulfite, 2-Nitroimidazole, Hydroxyurea, 5-Chloro-7-iodo-8-hydroxy-quinoline, Sulfanilamide, Trimethoprim, Dichlofluanid, Protamine sulfate, Chlorodinitrobenzene, Diamide, Cinoxacin, Streptomycin, Rifamycin SV, Potassium tellurite, Sodium Selenite, Glycine hydroxamate, 4-Chloro-3,5-dimethyl-phenol, D-Serine, Thiosalicylate, Salicylate, sodium, Sulfachloropyridazine, Oxycarboxin, 3-Amino-1,2,4-triazole, Chlorpromazine, Niaproof, Compound 48/80, Sodium Tungstate, Lithium chloride, Chlorambucil, Cefamandole nafate, Cefsulodin, Caffeine, Ketoprofen, Thiamphenicol, Trifluorothymidine, Poly-L-lysine, Pentachlorophenol, Sodium Arsenite, Lidocaine, Sodium periodate, Antimony (III) chloride, Semicarbazide hydrochloride, Tinidazole, 5-Fluoro-5'-deoxyuridine, 2-Phenylphenol, Plumbagin, Josamycin, Gallic acid, Methyltrioctylammonium chloride, 2,4-Dintrophenol, Chlorhexidine diacetate, trans-Cinnamic acid, Tetraethylthiuram disulfide, FCCP, D,L-Thioctic acid, Phenethicilllin, Sodium Caprylate, Lauryl sulfobetaine (N-Dodecyl-N,N-dimethyl-3-ammonio-1-propanesulfonate), Hexamine cobalt (III) chloride, Polymyxin B, Amitriptyline, Apramycin, Orphenadrine, D,L-Propanolol, Tetrazolium violet, Thioridazine, Atropine, Ornidazole, Proflavine, 18-Crown-6 ether, Crystal violet, Dodine (n-Dodecylguanidine), Hexachlorophene, 4-Hydroxycoumarin, Oxytetracycline, Pridinol, Captan, 3,5-Dinitrobenzoic acid, 8-Hydroxyquinoline, Patulin, Tolylfluanid, and Troleandomycin.

Resistance was observed in wells containing the following compounds with known antibacterial activity (at a maximum concentration of 4 ug): amikacin, lomefloxacin, bleomycin, colistin, gentamicin, ofloxacin, polymixin B, sulfamethazine, spectinomycin, ampicillin and oxolinic acid.

Example 6: Fatty Acid Composition

After incubation for 24 hours at 28° C., a loopful of well-grown cells were harvested and fatty acid methyl esters were prepared, separated and identified using the Sherlock Microbial Identification System (MIDI) as described (see Vandamme et al., 1992). The predominant fatty acids present in the *Bacillus megaterium* strains are shown in Table 2.

TABLE 2

Fatty Acid Methyl Ester (FAME) composition (%) of the different *Bacillus megaterium* strains with nematicidal activity.

| FAME | M018 | J142 | H491 |
|---|---|---|---|
| 14:0i | 4.77 | 6.05 | 6.36 |
| 14:0 | 1.33 | 1.65 | 1.52 |
| 15:0i | 41.89 | 32.97 | 32.03 |
| 15:0ai | 36.7 | 42.93 | 44.41 |
| 16:01☐7cOH | 1.32 | 1.39 | 1.03 |
| 16:0i | 0.97 | 1.41 | 2.11 |
| 16:1☐11c | 3.56 | 4.03 | 3.16 |
| 16:0 | 2.06 | 2.96 | 3.47 |
| 17:1☐10c | 1.38 | 0.56 | 1.95 |
| Sum in 4 | 1.08 | 0.71 | 3.97 |
| 17:0i | 2.22 | 1.89 | 1.95 |
| 17:0ai | 2.73 | 3.43 | 3.97 |
| Similarity index to B. megaterium | 0.949 | 0.948 | 0.991 |

Similarity indices of the FAME profiles to the database were all within the species confidence threshold (0.948-0.991). A dendogram was built by cluster analysis techniques to produce unweighted pair matching based on fatty acid compositions. The results indicate that H491 (listed as MBI-303) is most similar to J142, and that M018 is more different from the other two strains.

Example 7: Plant Growth Promotion Capabilities of B. megaterium H491

*B. megaterium* H491 was tested for plant growth promotion markers on five different plate assays, and representative results are shown in Table 11. The bacterium was able to solubilize phosphate and produced the enzyme ACC deaminase. It was also capable of growing on methanol as carbon source. These results suggested that *B. megaterium* H491 can promote growth and confer stress tolerance to plants.

Example 8: Growth Promoting Activity on Soy and Sorghum

To test for the ability of *B. megaterium* H491 to promote plant growth, two seedling vigor assays were performed on soy and sorghum. Strain H491 was grown on an agar plate and a few colonies were transferred to 50 ml sterile Luria broth (LB: 25 g/l) and incubated at 25° C., 180 rpm for 24 h. Bacterial cells were harvested from the LB cultures by centrifugation at 3220×g for 20 minutes. The supernatant was discarded and the cells were washed in 20 ml sterile $MgSO_4$ buffer then centrifuged for a second time at 3220×g for 20 minutes. After discarding the supernatant, the cells were re-suspended in a small volume of sterile buffer. The concentration of cells in the suspension was determined by measuring the absorbance at 600 nm in a spectrophotometer. Seeds were treated with the cell suspension by imbibition. A cell inoculum ($1 \times 10^8$ CFU/ml) was dispensed over the seeds, in a 50 ml Falcon tube, at a rate of 0.6 ml per gram of seed (for seed with 250-300 seed/g). The seed and inoculum were incubated overnight at 25° C., and treated seeds were then dried in a sterile hood for 30 min. The negative control was prepared in the same manner, except the cell inoculum was replaced with sterile buffer. Growth promotion was evaluated by measuring fresh weight of seedlings, as shown in Table 12. For soy, the seedling weight doubled with the H491 treatment. For sorghum, a 64% increase of the fresh weight was observed.

Example 9: Growth Promoting Activity on Corn

Corn seeds were planted and drenched at planting time and one week after planting with *B. megaterium* H491 whole cell broth (WCB). A total of 10 plants per pot and 9 pots per treatment were planted and evaluated. Total fresh weight was recorded 2 weeks after planting, and statistical analysis was performed using Minitab ANOVA Tukey's.

The results are shown in Table 13. In corn plants treated with H491 WCB, a significant increase in vegetative fresh weight was observed, with a 95% simultaneous confidence interval as assessed by Tukey's.

DEPOSIT OF BIOLOGICAL MATERIAL

The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Date of Deposit |
|---|---|---|
| *Bacillus megaterium* strain H491 | NRRL B-50769 | Aug. 3, 2012 |
| *Bacillus megaterium* strain M018 | NRRL B-50770 | Aug. 3, 2012 |
| *Bacillus megaterium* strain J142 | NRRL B-50769 | Aug. 3, 2012 |

The strain has been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

REFERENCES

Aksoy, H. M. and Ozman-Sullivan, S. K., 2008, Isolation of *Bacillus megaterium* from *Aphis pomi* (Homoptera: aphididae) and assessment of its pathogenicity *J. Plant Pathology* 90:449-452

Asolkar, R. N., Jensen, P. R., Kauffman, C. A., Fenical, W. 2006. Daryamides A-C, Weakly Cytotoxic Polyketides from a Marine-Derived Actinomycete of the Genus *Streptomyces* strain CNQ-085 *J. Nat. Prod.* 69:1756-1759.

Damberg, M., Russ, P., Zeeck, A. (1982). Die constitution der fungistatischen ansamycin-antibiotics ansatrienin A und B. *Tetrahedron Lett.* 23, 59-62.

Hebeda, R. E., Styrlund, C. R., Teague, W. M. (1988). Benefits of *Bacillus megaterium* amylase in dextrose production. *Starch* 40, 33-36.

Hu, X and Boyer, G. H. (1995). Isolation and characterization of the siderophore N-deoxyschizokinen from *Bacillus megaterium* ATCC 19213. *BioMetals*, 8, 357-64 (Japan. Pat., 83 164 561. (1983)).

Izawa, M., Wada, Y., Kasahara, F., Asai, M., Kishi, T. (1981. Hydroxylation of ansamitocin P-3. *J. Antibit.*, 34 1591-1595.

Kittsteiner-Eberle, R., Ogbomo. I., Schmidt, H. L. (1989). Biosensing devices for the semi-automated control of dehydrogenase substrates in fermentations. *Biosensors* 4, 75-85.

Komatsu, Y., Hayashi, H. (1998). Histone deacetylase inhibitors up-regulate the expression of cell surface MHC class-I molecules in B16/BL6 cells. *J. Antibiot.* 51, 89-91.

Martin, L., Prieto M. A., Cortes, E., Garcia, J. L. (1995). Cloning and sequencing of the pac gene encoding the penicillin G acylase of *Bacillus megaterium* ATCC 14945. *FEMS Microbiol Lett* 125, 287-292.

Metz, R. J., Allen, L. N., Cao, T. M., Zeman, N. W. (1988). Nucleotide sequence of an amylase gene from *Bacillus megaterium. Nucleic Acids Res.* 16, 5203.

Nagao, T., Mitarnura, T., Wang, X. H., Negoro, S., Yorno, T., Urabe, I., Okada, H. (1992). Cloning, nucleotide sequences, and enzymatic properties of glucose dehydrogenase isozymes from *Bacillus megaterium* IAM1030. *J. Bacteriol.* 174, 5013-5020.

Nakahama, K., Izawa, M., Asai, M, Kida, M., Kishi, T. (1981). Microbial conversion of anamitocin. *J. Antibiot.*, 34 1581-1586.

Nithya, C., Devi, M. G., Pamdian, S. K. 2011. A novel compound from the marine bacterium *Bacillus pumilus* S6-15 inhibits biofilm formation in gram-positive and gram-negative species. *Biofouling*, 27, 519-528.

Plowman, J. E., Loehr, T. M., Goldman, S. J., Sanders-Loehr, J., (1984). Structure and siderophore activity of ferric Schizokinen. *J. Inorg. Biochem.*, 20, 183-186.

Shimada, N., Hasegawa, S., Harada, T., Tomisawa, T., Fujii, A., Takita, T. (1986). Oxetanocin, a novel nucleoside from bacteria, *J. Antibiot.*, 39, 1623-1625.

Shimada, N., Hasegawa, S., Saito, S., Nishikiori, T., Fujii, A., Takita, T. (1987). Derivatives of oxetanocin: oxetanocins H, X, G and 2-aminooxetanocin A. *J. Antibiot.*, 40, 1788-1790.

Suga, K., Shiba, Y., Sorai, T., Shioya, S., Ishimura, F. (1990). Reaction kinetics and mechanism of immobilized penicillin acylase from *Bacillus megaterium. Ann N Y Acad Sci.* 613, 808-815.

Takaichi, S. (1990). Heterogeneous position of the double bonds of unsaturated fatty acids in carotenoid glucoside esters from *Rhodococcus rhodochrous* RNMS1. *Agric. Biol. Chem.*, 54, 2139-2140.

Takasaki, Y. (1989). Novel maltose-producing amylase from *Bacillus megaterium* G-2. *Agric Biol Chem.* 53, 341-347.

Vandamme et al. Polyphasic taxonomic study of the emended genus *Arcobacter* with *Arcobacter butzleri* comb. nov. and *Arcobacter skirrowii* sp. nov., an aerotolerant bacterium isolated from veterinary specimens." Int. J. Syst. Bacteriol. 42: 344-356. 1992.

Vihinen, M., Mantsala, P. (1989). Microbial amylolytic enzymes. *Crit Rev Biochem Mol Biol.* 24, 329-418.

What is claimed is:

1. A method for inducing drought tolerance in a plant comprising the steps of:
    contacting said plant and/or its seed and/or its growth substrate with a composition comprising a whole cell broth, collected from a *Bacillus megaterium* strain H491 (NRRL Accession No. B-50769) fermentation, in an amount effective to increase said drought and/or salt tolerance of said plant.

2. The method according to claim 1, wherein said plaint is selected from the group consisting of strawberry, squash, cucumber, tomato, rose, pepper, eggplant, grapevine, cotton, onion, garlic, wheat, soy, corn and rice.

3. The method according to claim 1, further comprising transplanting said plant into said growth substrate.

4. The method according to claim 3, wherein prior to transplanting said plant into said growth substrate, one or more roots of said plant are treated with said composition.

5. The method according to claim 1, wherein said composition comprises further comprises a biological drought tolerance inducing agent comprising *Bacillus* sp., *Paecilomyces* sp., *Pasteuria* sp., *Pseudomonas* sp., *Brevabacillus* sp., *Lecanicillium* sp., *Ampelomyces* sp., *Pseudozyma* sp., *Streptomyces* sp, *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorospirmium*, *Neobulgaria*, *Daldinia*, *Aspergillus*, *Chaetomium*, *Lysobacter* spp., *Lachnum papyraceum*, *Verticillium suchlasporium*, *Arthrobotrys Oligospora*, *Verticillium chlamydosporium*, *Hirsutella rhossiliensis*, *Pochonia chlamydosporia*, *Pleurotus Ostreatus*, *Omphalotus Olearius*, *Lampteromyces japonicas*, *Brevudi monas* sp., and/or *Muscodor* sp.

* * * * *